United States Patent [19]

Gartz

[11] Patent Number: 5,476,106

[45] Date of Patent: Dec. 19, 1995

[54] METHOD OF DESTROYING AND STORING USED CANNULAS

[75] Inventor: Kaj Gartz, Orange, Conn.

[73] Assignee: Owen J. Meegan, Salem, Mass.; a part interest

[21] Appl. No.: 662,475

[22] Filed: Feb. 28, 1991

Related U.S. Application Data

[63] Continuation-in-part of Ser. No. 621,287, Nov. 30, 1990, Pat. No. 5,084,020, and Ser. No. 657,529, Feb. 19, 1991, Pat. No. 5,084,019.

[51] Int. Cl.⁶ .................................................. A61B 19/00
[52] U.S. Cl. ......................... 128/898; 128/919; 604/110; 604/240
[58] Field of Search .................... 239/195, 198; 128/919, 763, 898; 604/280, 264, 177, 240, 243, 110, 197, 188

[56] References Cited

U.S. PATENT DOCUMENTS

| | | |
|---|---|---|
| 3,472,456 | 10/1969 | Strong . |
| 3,747,812 | 7/1973 | Karmen et al. . |
| 3,893,608 | 7/1975 | Koening . |
| 4,266,544 | 5/1981 | Wardlaw ................................. 604/110 |
| 4,273,123 | 6/1981 | Lemelson . |
| 4,342,313 | 8/1982 | Chittenden ............................... 604/280 |
| 4,582,257 | 4/1986 | Siegler ..................................... 239/198 |
| 4,634,428 | 1/1987 | Cuu . |
| 4,804,370 | 2/1989 | Haber et al. ............................ 604/110 |
| 4,925,450 | 5/1990 | Imonti et al. ........................... 604/240 |
| 4,932,939 | 6/1990 | Magre et al. ........................... 604/195 |
| 4,986,813 | 1/1991 | Blake, III et al. ...................... 604/195 |
| 5,019,048 | 5/1991 | Margolin ................................. 604/192 |
| 5,084,019 | 1/1992 | Gartz ....................................... 604/192 |
| 5,084,020 | 1/1992 | Gartz ....................................... 604/192 |

*Primary Examiner*—C. Fred Rosenbaum
*Assistant Examiner*—Ronald K. Stright, Jr.

[57] ABSTRACT

A method of destroying and storing a cannula adapted to contact bodily fluids. According to the method, a cannula having at least one sharp point is disposed in an operative relationship with a reel which is fitted in a housing. A portion of the cannula extends exteriorly of the housing and is slidably disposed within an aperture in the housing. A portion of the cannula that is disposed within the housing engages the reel when it is turned and bends the cannula to destroy it and simultaneously commences drawing the cannula into the housing through the aperture to store it. The turning is continued until the point is fully withdrawn into the housing. When fully withdrawn, the point(s) of the cannula snap against the inside of the housing and provide a sensory indication that they are fully withdrawn.

15 Claims, 4 Drawing Sheets

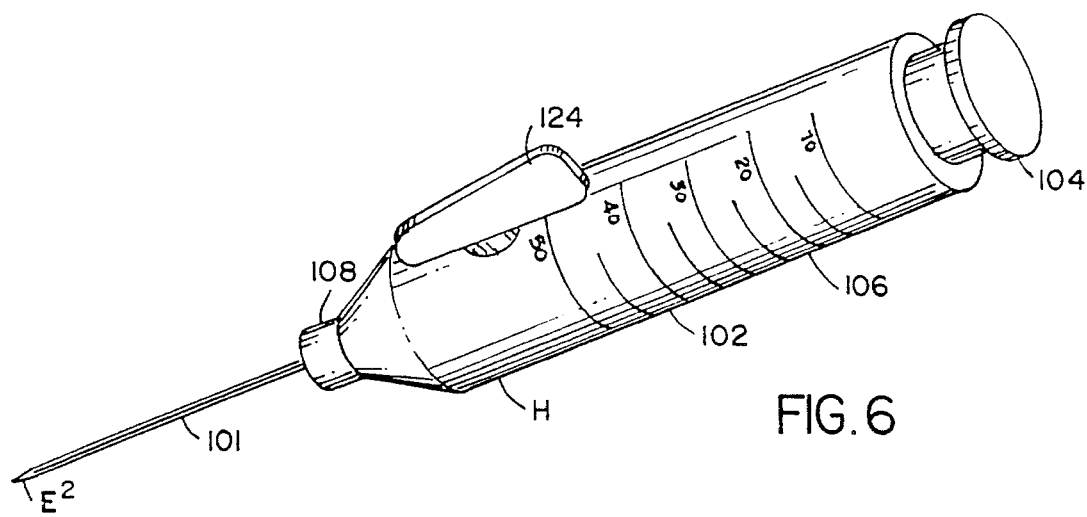
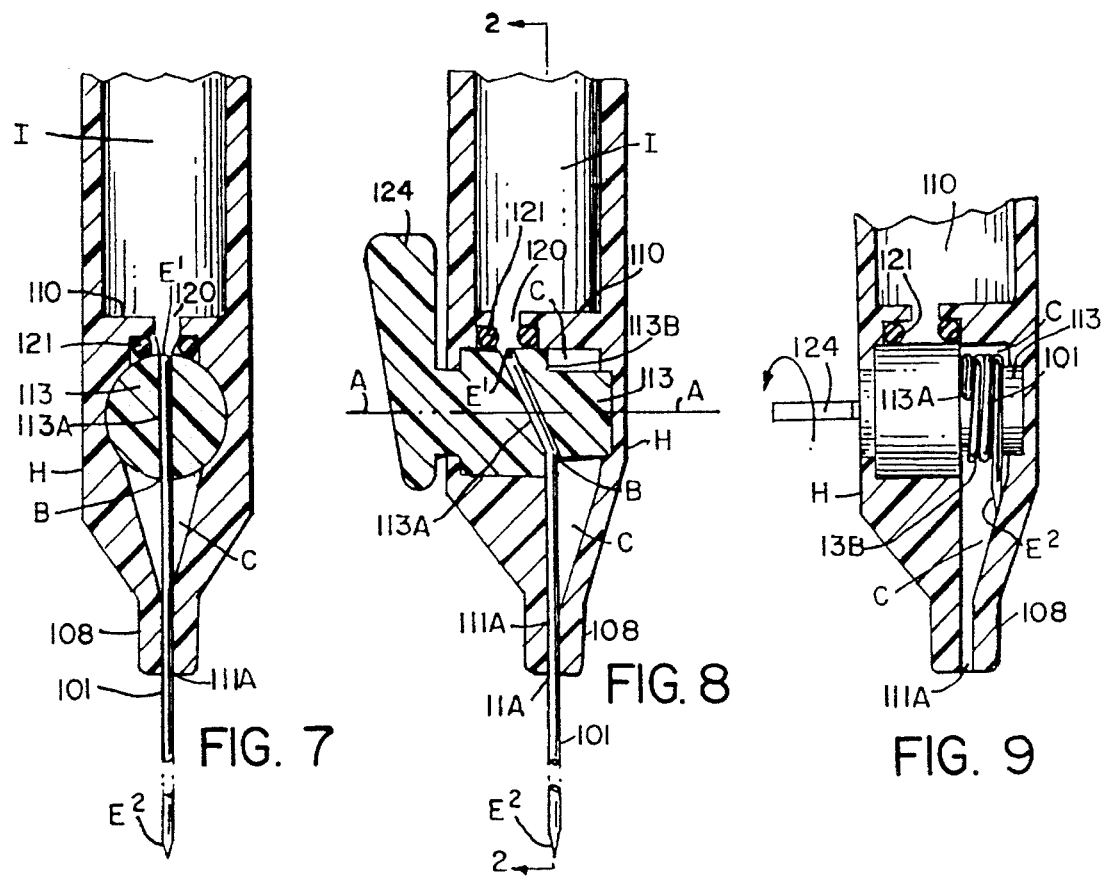

METHOD OF DESTROYING AND STORING USED CANNULAS

RELATION TO OTHER APPLICATIONS

This application is a continuation in part of my applications, Ser. No. 621,287, filed Nov. 30, 1990 now U.S. Pat. No. 5,084,020 and Ser. No. 657,529, filed Feb. 19, 1991 now U.S. Pat. No. 5,084,019.

BACKGROUND OF THE INVENTION

The present invention relates to a method of employing a device embodying a cannula so as to insure the cannula's destruction and safe storage after use. The method is especially useful for needles that have come into contact with human blood and which are adapted to be used only once.

Cannulas and equipment used for sampling blood and injecting therapeutic fluids frequently are disposable and designed to be discarded after a single use. Once a cannula has been used to draw blood or inject a medication, it is contaminated. The sharp point on a contaminated needle can injure people and cause the spread of disease among those that handle it. Infectious diseases such as HIV or hepatitis viruses have been transmitted to people who handle contaminated needles and accidentally stick themselves with them. Small residues of blood and viruses on the cannula from an infected patient can result in transmission of a disease that the patient has contracted to a staff member.

In the past, relatively complex arrangements have been devised to prevent the accidental infections from contaminated needles. I have found that destruction of the cannula and covering its sharp point(s) is highly desirable because hypodermic needles are frequently reused by drug abusers and accidental contact or intentional use must be eliminated.

Exemplary of devices which have attempted to solve these problems is the application of Ameur: Int. Pub. No. WO89/11304; PTC/SE89/00290. The application discloses a pair of protective sleeves that are displaceable in a longitudinal direction over a holder that is provided for a double pointed cannula. The sleeves serve as adapters that provide a bayonet socket which is fitted into another bayonet socket. The arrangement is used with a sample holder which has steps formed in an end to receive a peg that holds the arrangement together during use. As viewed, the sleeves of the cannula can easily move and expose the needle after use when it is contaminated. Moreover, the arrangement requires the provision for a specially designed sample holding device to accommodate the sleeves and even with this fairly complex combination, the needle is not destroyed after use.

In the United States Patent to Wardlaw, U.S. Pat. No. 4,366,544, patentee describes a hypodermic syringe which has provision for preventing more than one use and rendering the needle inoperative. According to the Wardlaw patent, a mechanism is mounted on the syringe which, after administering the injection, is manipulated to bend the needle of the syringe at a right angle and concurrently retract it from its normally projecting position to a second position in which it is housed in a cavity. The retraction is accomplished by twisting a cap around a post so that the needle is permanently deformed and wrapped around the post. while protection of the needle point and destruction of the needle is provided with the mechanism, significant torque is required to twist the cap to urge the needle around the post to destroy and house it. The amount of torque necessary to accomplish the wrapping and housing can exceed the strength of the various plastic parts.

Capping arrangements such as shown in Lemelson, U.S. Pat. No. 4,273,123; Karmen et al, U.S. Pat. No. 3,747,812; and Cuu, U.S. Pat. No. 4,634,428, all involve an ancillary cap over the cannula to bend or distort the metal. Similarly, the U.S. patent to Koening, U.S. Pat. No. 3,893,608, discloses a syringe that is fitted onto a cover to distort it through the placement of a post surrounding by an annular ring.

SUMMARY OF THE INVENTION

According to the present invention, I have found that if I dispose a cannula in a hollow housing and through a reel that is fitted in the housing that I can enable the user to simultaneously destroy the cannula, store it and prevent accidental contact with the sharp points of the needle. The housing is preferably formed of molded styrene, polycarbonates, polyamides or polyethylene. After use, a portion of the cannula disposed within the housing engaged by the reel which is turned to draw the point(s) into a containment area in the housing and wrap the cannula around it whereby the exposed point(s) of the cannula are stored in the housing. In one embodiment (with a double pointed needle) when the reel is turned, both ends of the needle are simultaneously drawn into the housing and the cannula is wrapped around the reel. The wrapping causes the sharp points also to be drawn into the containment area and safely stored. when completely drawn into the housing. I have further found that a positive indication of complete covering of the sharp point(s) is provided by the feel and sound of them snapping against the inside of the housing which indicates that the device is safe to be disposed of without injury. In another embodiment, with single ended needles useful with hypodermic syringes, the single point is similarly drawn into a housing and wrapped onto the reel.

BRIEF DESCRIPTION OF THE DRAWINGS

FIG. 6 is a perspective view of another embodiment of a hypodermic syringe that can be used with the method of the present invention;

FIG. 7 is a cross-sectional view of an embodiment of the invention in which a needle having one point is disposed within a housing and through the reel;

FIG. 8 is a cross-sectional view of the embodiment shown in FIG. 7. This view shows the syringe turned 90°;

FIG. 9 is an enlarged fragmentary view of the reel shown in FIG. 8. In this view, the cannula is wrapped about the reel, destroyed and safely stored within the housing;

Figure 10:
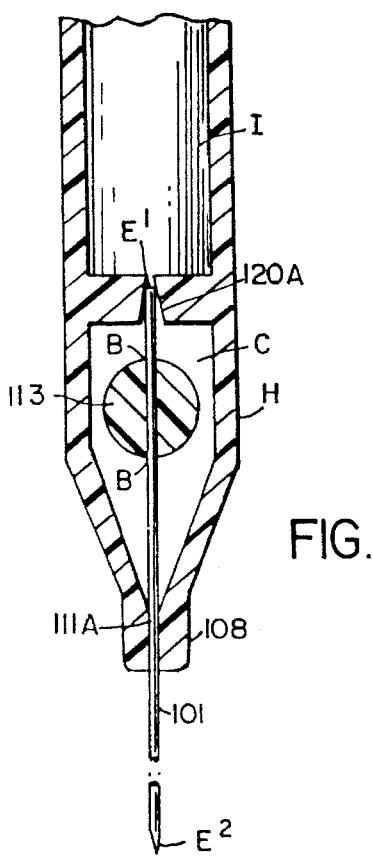
FIGS. 10 and 11 are cross-sectional views of another embodiment that can be used with the method of the present invention. In this embodiment, the end of the cannula is detachably disposed within a bottom wall of the hypodermic syringe and through a reel. The Figures are of the same embodiment, except that the cross sections are offset from each other by 90°.
Figure 11:
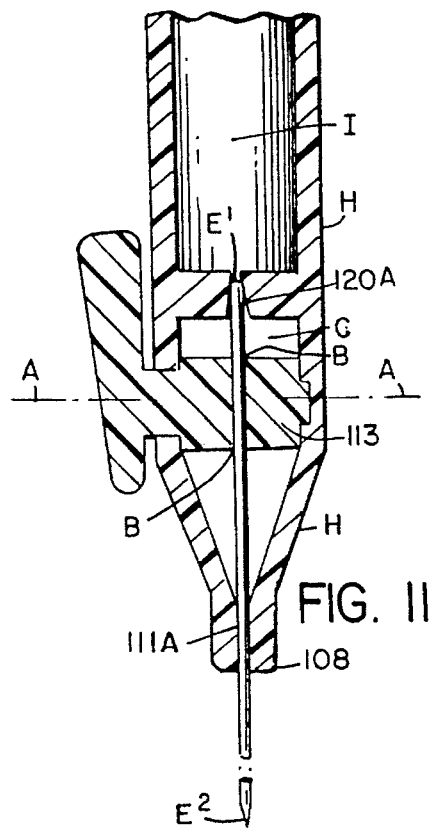
Figure 12:
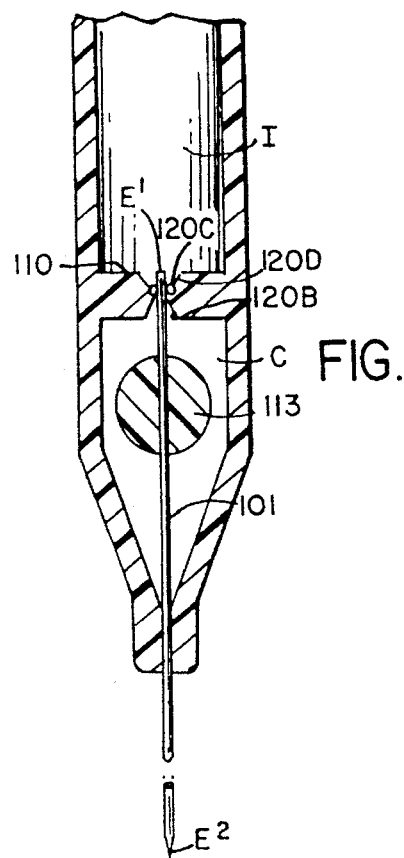
Figure 13:
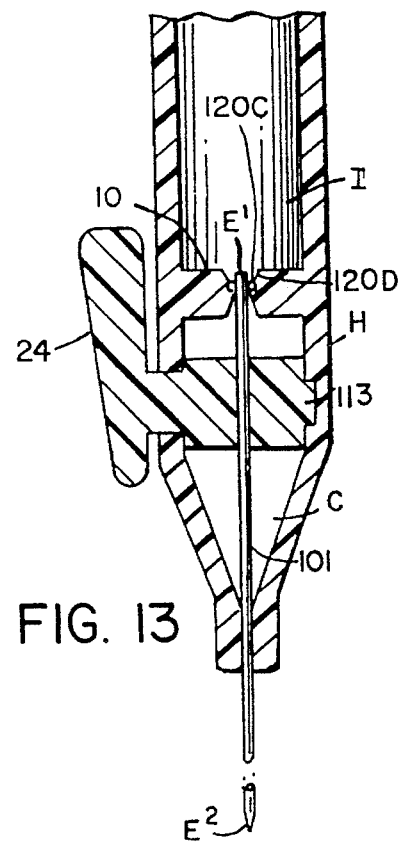

The embodiment shown in FIGS. 12 and 13 are similar to the embodiment shown in FIGS. 10 and 11, except that an end of the cannula is seated in the bottom wall of the hypodermic syringe with an adhesive. One view is offset from the other by 90°.

DESCRIPTION OF THE PREFERRED EMBODIMENTS

Figure 1:
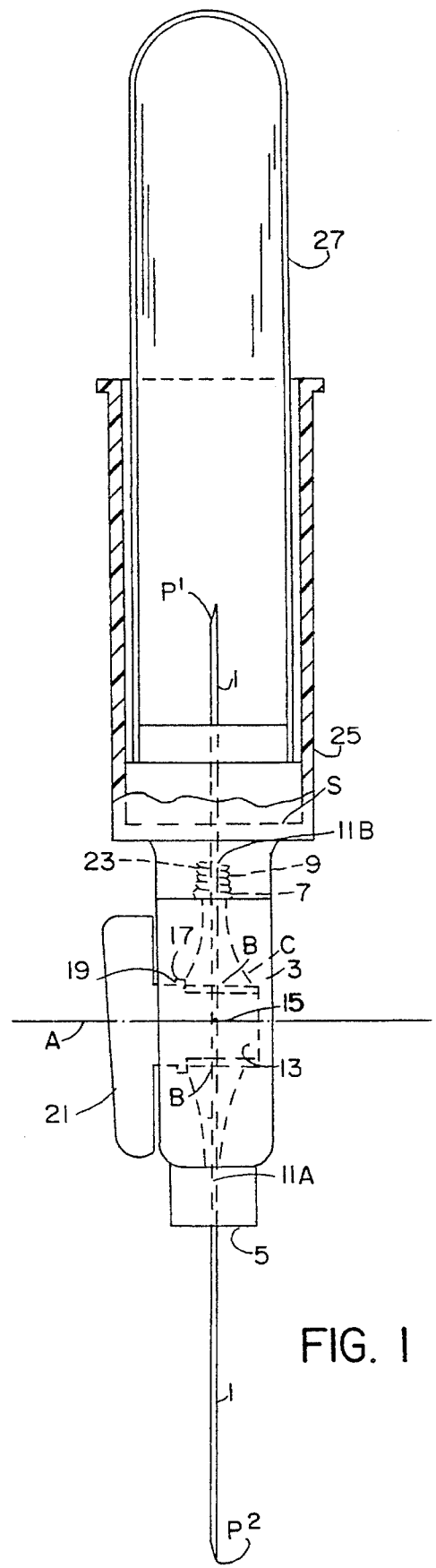
FIG. 1 is a side elevational view, partially in cross-section, of an embodiment of the disposable device that can be used with the method of the present invention.

Referring now to FIG. 1, a cannula 1 having sharp end points, herein called dispensing point $P^1$ and receiving point $P^2$, is shown fitted in a housing 3. The housing 3 has a first end 5 and a second end 7. The second end 7 terminates in a threaded nipple 9. One end of the cannula 1 is slidably disposed in an aperture 11A that is formed in the first end 5 and the other end of the cannula 1 slidably disposed in another aperture 11B that is formed in the second end 7.

The cannula 1 is fixedly disposed in a throughhole 15 that is formed in a reel 13. Reel 13 is rotatably disposed in the housing 3 and rotates about an axis A. The axis of rotation of the reel 13 is preferably at right angles to the cannula 1 so that when the reel 13 is turned on its axis, the cannula 1 bends at points B and then wraps around reel 13. Since cannula 1 is slidably disposed within the apertures 11A and 11B, the points $p^1$ and $P^2$ can be retracted into housing 3.

Preferably, a flange 17 is disposed on the side of the reel 13 and fits into a recess 19 to insure easy rotation and to prevent the reel 13 from falling out of the housing. A handle 21 is attached to reel 13 to enable the user to turn it. In the embodiment shown, the threaded nipple 9 is screwed into an internally threaded end 23 of a conventional holder 25. A conventional vacuum tube 27 is shown with a stopper S is fitted into its open end. In use, the receiving point $P^2$ is inserted into a patient's blood vessel. Dispensing point $p^1$ of cannula 1 is forced through stopper S and blood will pass through the receiving point $P^2$ into the cannula 1 to emerge from the dispensing point $P^1$ and into the vacuum tube 27. A multiplicity of different vacuum tubes 27 are frequently used in medical facilities and they are serially disposed on cannula 1 to take samples for different tests. After the required number of samples have been taken, the last vacuum tube is removed from the holder 25 and the cannula 1 is withdrawn from the patient. The handle 21 is then turned on axis A to cause the cannula 1 to wrap around the reel 13 and withdraw through apertures 11A and 11B, as will be described hereinafter.

Figure 2:
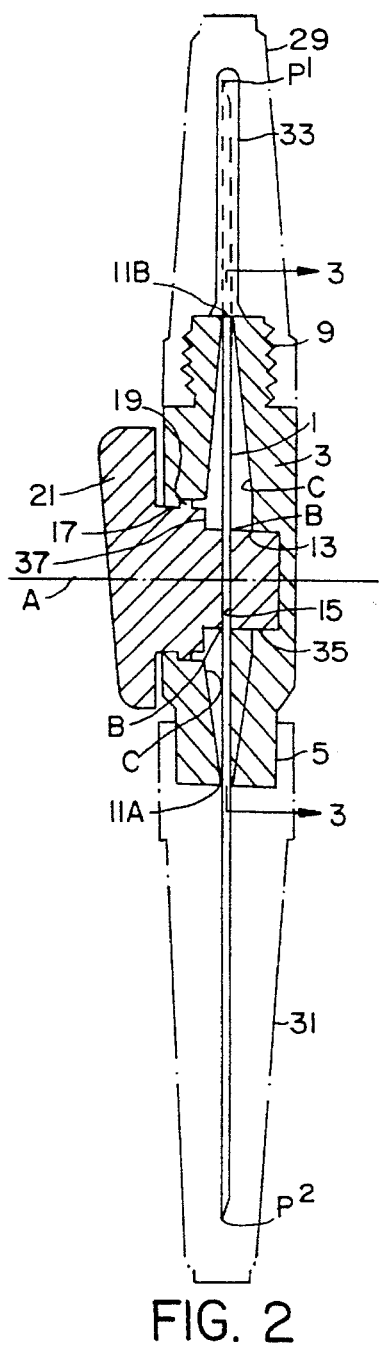
FIG. 2 is an elevational view, partially in cross section, of the embodiment shown in FIG. 1. This view also shows caps that are placed over the sharp points of the device to aid in safe handling before use.

Referring now to FIG. 2, the device of the present invention is shown in cross-section. The device includes the housing 3 in which is disposed the cannula 1. A cavity C is formed within the housing 3 to provide room for the wrapped cannula 1. As shown, a cover 29 fits over the dispensing point $P^1$ and another cover 31 fits over the receiving point $P^2$. Cover 31 is slidably disposed over first end 5 and cover 29 is threaded onto nipple 9. As is well known, usually a rubber shield 33 is fitted over dispensing point $P^1$. When a vacuum tube is forced over dispensing point $P^1$ the rubber shield 33 is urged back and slides along cannula 1 ahead of the stopper to prevent blood from leaking from the end of the dispensing point $P^1$ as vacuum tubes are being changed to secure samples. When one vacuum tube is removed and before another is put on, the shield 33 will slide back into its original position to cover point $P^1$ and then will slide back ahead of the next stopper that is to be filled.

As mentioned previously, the reel 13 is rotatably disposed within the housing 3. One side of the reel 13 is disposed within the fitting 35 that is formed inside of the housing 3 and the other side has flange 17 that is disposed within recess 19. A shoulder 37 is formed on the side of reel 13 to receive the cannula 1 as it is being destroyed by twisting handle 21 after use. The cannula 1 is fixedly disposed in the throughhole 15 so that when the point $P^2$ is being inserted into the patient being tested, it will not slide upwardly. Also, the fixed disposition of cannula 1 in throughhole 15 prevents the point $P^1$ from moving as a vacuum tube is forced onto it. Such fixed disposition can be easily accomplished by using well known adhesives that bind metal to plastic or the reel can be simply molded around the cannula.

Figure 3:
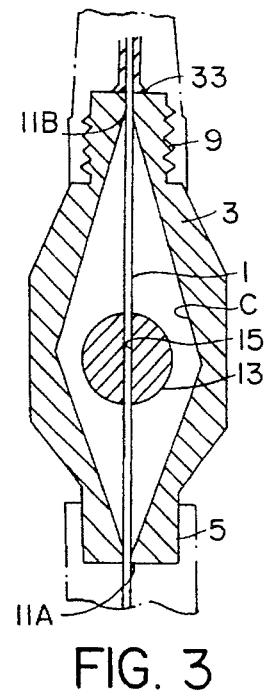
FIG. 3 is cross-sectional view taken along the lines 3—3 of FIG. 2.

As shown in FIG. 3, the cannula 1 is disposed in the throughhole 15 that preferably passes through the diameter of the reel 13. As set out previously, cannula 1 is preferably disposed at right angles to the axis of rotation A of reel 13. Containment area C is large enough to receive all of the destroyed cannula 1. Containment area C preferably is shaped so that there is a greater amount of freeboard space on the longitudinal axis than on the lateral axis.

Figure 4:
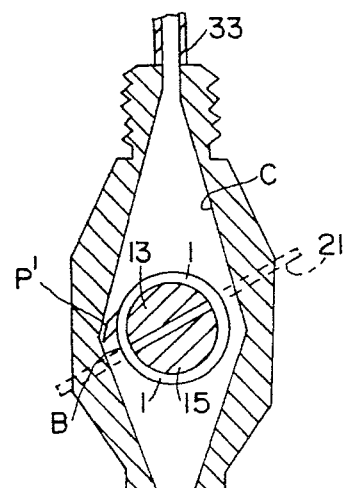
FIG. 4 is the same cross-sectional view taken as FIG. 3, except that in FIG. 4, the cannula is shown destroyed and safely stored within the device.

As shown in FIG. 4, the internal shape of containment area C causes the point $P^1$ (and $P^2$, not shown) to engage and then disengage the sides so that when the handle 21 is turned to wrap cannula 1 around reel 13 and the point $P^1$ (and $P^2$) is fully retracted, it snaps against the inside to produce sensory indications of full withdrawal. The used, destroyed cannula 1 is thus wrapped and safely stored on reel 13. In the illustration, a clockwise rotation of the handle 21 is shown but counterclockwise rotation is equally effective. When the points $P^1$ and $P^2$ are fully retracted into the housing 3 the device can be readily handled without fear of them accidently sticking the person who is working with it. If desired, the cover 29 over point $P^1$ and the cover 31 over point $P^2$ can be redisposed on the device but such redisposition is not necessary.

Figure 5:
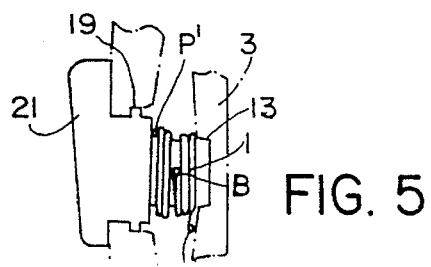
FIG. 5 is a view of the reel and handle shown in FIG. 4 (turned 90°) with the destroyed cannula wound upon the reel and safely stored.

As shown in FIG. 5, the cannula 1 is wrapped around reel 13. Cannula 1 emerges from throughhole 15 and wraps initially at bend B. while a neat winding of the cannula 1 is shown around reel 13, such neat disposition of the cannula 1 is not necessary and it may not even occur. The number of turns necessary to fully retract points $P^1$ and $P^2$ into the housing is a function of the length of the cannula 1 and the diameter of the reel 13 and may be varied as desired.

Referring now to FIG. 6, a cannula 101 is shown together with a hypodermic syringe 102. A plunger 104 is disposed within the transparent barrel 106, as is well known. The lower end of the hypodermic syringe includes a reel that is rotatably disposed inside a housing H (and shown in enlarged cross-sectional views in FIGS. 7 to 13). A handle 124 is integrally attached to the reel so that twisting the handle 124 will turn the reel and cause cannula 101 to be withdrawn through an aperture in a nose 108 of the housing H for destruction and storage.

Referring to FIGS. 7, 8 and 9, the cannula 101 is shown having two ends (herein called a receiving end $E^1$ and a dispensing end or point $E^2$). Part of the cannula 101 is disposed in a hollow housing H. The nose 108 of the housing H has the general shape of a nipple with an opening 111A to receive the cannula 101. The top of housing H is formed beneath a bottom wall 110 of the hypodermic syringe which also forms the bottom of the interior I of the syringe.

The cannula 101 is slidably disposed in the aperture 111A in the nose 108 and extends outwardly therefrom for use in injecting medications. Another portion of the cannula 101 is fixedly disposed within a throughhole 113A that is formed in reel 113. Such fixed disposition of cannula 101 can be accomplished by many means which can include the application of adhesive or simply molding the reel 113 about the cannula 101. Reel 113 is rotatably disposed within the housing H can be rotated about an axis A—A which is preferably at right angles to the cannula 101 so that when the reel 113 is turned, it bends at point B and then wraps around the reel 113 (as shown in FIG. 9). Reel 113 is surrounded by a containment area C. Since cannula 101 is slidably disposed within aperture 111A, as the point $E^2$ is retracted into a containment area C in the housing H it is safely stored.

The interior I of the hypodermic syringe is in fluid flow communication with a lumen in the cannula 101 by means of an opening 120 disposed in the bottom wall 110. The opening 120 has a step adjacent the reel 113 to receive an O-ring 121 that surrounds it and urges against the reel 113 to prevent leakage into the spaces between the reel 113 and the interior of the housing H. Upon application of pressure to plunger, the medication will be urged into the lumen of cannula 101 to flow out of point $E^2$ of cannula 101. On the other hand, when fluids such as blood are to be withdrawn from a patient, the withdrawal of plunger from the interior I of the hypodermic syringe will cause the blood flow into point $E^2$ and emerge at end $E^1$ to flow into the interior I of the hypodermic syringe. In this embodiment, the end $E^1$ of the cannula 101 is shown to be substantially flush with the outside of the reel 113 to enable reel 113 to be turned easily about its axis. In other embodiments, however, the flush disposition of end $E^1$ relative to reel 113 may not be necessary, as will be seen hereinafter.

As shown in FIG. 8, reel 113 is fitted in housing H so that the end with the handle 124 passes through a side wall and the other end is rotatably disposed in the opposite side wall. A step 113B is formed on reel 113 to provide for a space between reel 113 and containment area C for storage of the cannula 101.

As shown in FIG. 9, the containment area C provides space for the cannula 101 when it is wound upon reel 113. Point $E^2$ is safely stored within containment area C and cannot be touched after the cannula 101 is wound. At the same time, the O-ring 121 continues to urge against the portion of the reel 113 having the larger diameter to prevent the seepage of fluids.

As shown in FIG. 8, the cannula 101 is bent at point B at an angle necessary to place end $E^1$ beneath opening 120 in the bottom wall 110. Bending the cannula 101 at the predetermined angle enables the O-ring 121 to cover the area around cannula 101 where it emerges from the reel 113. The angle that the cannula 101 is bent is not critical so long as the end $E^1$ is disposed beneath the opening 120 and the O-ring 121. The longitudinal axis of the cannula 101 is at right angles to the axis of rotation A—A of the reel 113.

Referring now to FIGS. 10 and 11, another embodiment of the invention is shown. In this embodiment, the cannula 101 extends into a generally conically shaped opening 120A having a very narrow apex angle. The end $E^1$ of the cannula 101 is snugly force fit into the opening 120A (which is drawn somewhat exaggerated in order to show the conical shape). The essential feature, however, is that the cannula 101 is detachably removable from the opening 120A and will not allow the flow of fluids from the interior I of the syringe into the containment area C while the plunger is being pushed. As in the previous embodiment, the point $E^2$ extends from the nose 108 of the housing H. Upon turning reel 113 with handle 124 about axis A—A, the cannula 101 will bend at points B and will wrap itself around reel 113. End $E^1$ will be drawn through opening 120A and simultaneously point $E^2$ will be drawn up into aperture 111A in the nose 108. Continued twisting of the reel 113 about its axis will eventually cause the point $E^2$ to be fully withdrawn into containment area C. When the cannula is fully withdrawn into containment area C, point $E^2$ will snap against its interior walls, thereby giving an audible and tactile sensation that it is fully withdrawn and safely stored.

Another embodiment of the present invention is shown in FIG. 12 and 13. This embodiment is substantially the same as the one shown in FIGS. 10 and 11, except that cannula 101 extends through the opening 120B in bottom wall 110 and is detachably held in place by a small dab of adhesive 120C or with an O-ring or washer that has been snugly fitted over the end $E^1$ and will butt with an aperture 120D so as to prevent leakage into or from the interior I of the syringe. Twisting reel 113 about its axis A—A will break the adhesive bond (or remove the cannula 101 from the O-ring or washer) in opening 120B.

It is apparent that modifications and changes can be made within the spirit and scope of the present invention but it is my intention, however, only to be limited by the scope of the appended claims.

As my invention, I claim.

1. A method of rendering harmless a cannula used for injections, a first portion of said cannula being disposed within a housing and a second portion extending outwardly therefrom and terminating in an end, said method comprising the steps of:

disposing part of said first portion of said cannula in a rotatable reel;

turning said reel about an axis to draw said second portion of said cannula into said housing to destroy said cannula and store it within said housing.

2. The method according to claim 1 wherein the axis of rotation of said reel is at right angles to the disposition of said cannula and including the step of drawing said cannula at right angles to said axis.

3. The method according to claim 1 wherein said housing is hollow and including the steps of retracting said cannula into said hollow housing and tactilely and/or audibly observing snapping of said end of said cannula against the inside of said housing to receive sensory indications that the cannula is destroyed and stored.

4. The method according to claim 1 including the steps of winding said cannula around said reel to retract said cannula within said housing, thereby to completely withdraw and safely store it.

5. A method of destroying and storing a cannula adapted to contact bodily fluids, said method comprising:

disposing a cannula having two sharp points at the ends thereof in a fixed relationship within a storage means, said storage means being disposed within a housing, a portion of said cannula extending exteriorly of said housing through apertures formed in said housing, said points being disposed outside of said housing and said cannula being slidably arranged within said apertures;

engaging portions of the cannula with said storage means and bending said cannula and simultaneously commencing drawing said cannula into said housing through said apertures;

continuing said engagement until said points are fully withdrawn into said housing whereby to destroy said cannula and store it within said housing.

6. The method according to claim 5 wherein the storage means has an axis of rotation and including the step of rotating said storage means about said axis to engage said cannula and to deform and store the deformed cannula.

7. The method according to claim 6 wherein said cannula is disposed normal to said axis of rotation and including the step of drawing said cannula into said housing at right angles to said axis.

8. The method according to claim 6 wherein said cannula is fixedly disposed relative said axis and said storage means is rotatably receivable of said cannula and including the step of rotating said storage means about said axis and retracting said cannula and said points into said housing and around said storage means.

9. The method according to claim 6 wherein the axis of rotation of said storage means is at right angles to the path of retraction of said cannula.

10. The method according to claim 5 wherein said housing is hollow and further including the steps of fully retracting the points of said cannula into said hollow housing and tactilely and/or audibly observing the snapping of the points against the inside of said hollow housing to receive sensory indications that the cannula is destroyed and fully withdrawn.

11. The method according to claim 5 wherein said storage means is a reel further including the step of turning said reel and wrapping said cannula around said reel for destruction and storage thereof.

12. A method of using, destroying and safely storing a cannula having at least one sharp point, said method including:

disposing a part of a first portion of said cannula in a reel, said reel being disposed in a housing with a second portion of said cannula and said sharp point being disposed outside of said housing;

using said cannula and after use, engaging a part of said first portion of said cannula with said reel;

turning said reel and simultaneously deforming said cannula and wrapping it around said reel whereby to draw said sharp point into said housing to destroy and store it.

13. The method according to claim 12 wherein said cannula is drawn into said housing at right angles to the axis of rotation of said reel.

14. A method of destroying and storing a cannula having at least one sharp point, said method including:

disposing a first portion of a cannula within a storage means, said storage means having an axis of rotation, said cannula being fixedly disposed relative to said axis, said storage means being disposed within housing, a second portion of said cannula extending from said storage means exteriorly of said housing and being slidably disposed within an aperture in said housing;

rotating said storage means about said axis and engaging a part of said first portion of said cannula with said storage means and wrapping said cannula around said storage means and simultaneously commencing drawing said second portion of said cannula into said housing at right angles to said axis;

continuing said engagement until said point is fully withdrawn into said housing whereby said storage means destroys and stores said cannula within said housing.

15. The method according to claim 14 wherein said housing is hollow and wherein when the point of said cannula is fully withdrawn into said hollow housing, the step of tactilely and/or audibly observing the snapping of the point against the inside of said hollow housing to receive sensory indications that it is destroyed and fully withdrawn.

* * * * *